United States Patent
Renquist (10) Patent No.: US 12,210,013 B2
(45) Date of Patent: Jan. 28, 2025

(54) METHODS AND SYSTEMS FOR MEASURING GROWTH RATE IN PLANT OR AQUATIC ANIMAL SPECIES

(71) Applicant: ARIZONA BOARD OF REGENTS ON BEHALF OF THE UNIVERSITY OF ARIZONA, Tucson, AZ (US)

(72) Inventor: Benjamin J. Renquist, Tucson, AZ (US)

(73) Assignee: ARIZONA BOARD OF REGENTS ON BEHALF OF THE UNIVERSITY OF ARIZONA, Tucson, AZ (US)

(*) Notice: Subject to any disclaimer, the term of this patent is extended or adjusted under 35 U.S.C. 154(b) by 757 days.

(21) Appl. No.: 17/394,933

(22) Filed: Aug. 5, 2021

(65) Prior Publication Data

US 2021/0364501 A1 Nov. 25, 2021

Related U.S. Application Data

(62) Division of application No. 15/754,126, filed as application No. PCT/US2016/048006 on Aug. 22, 2016, now abandoned.

(Continued)

(51) Int. Cl.
*G01N 33/52* (2006.01)
*A01K 67/02* (2006.01)
(Continued)

(52) U.S. Cl.
CPC .............. *G01N 33/52* (2013.01); *A01K 67/02* (2013.01); *C12Q 1/008* (2013.01);
(Continued)

(58) Field of Classification Search
CPC .............. G01N 33/52; G01N 33/1806; G01N 33/5005; G01N 33/5088; G01N 33/5097;
(Continued)

(56) References Cited

U.S. PATENT DOCUMENTS

2004/0261143 A1* 12/2004 Mumm .............. C12N 15/8509
                                                          800/20
2007/0015164 A1   1/2007 Khatib
(Continued)

FOREIGN PATENT DOCUMENTS

EP            333790      7/2021
KR     20140140904 A     12/2014
(Continued)

OTHER PUBLICATIONS

Allee et al. "Some effects of social organization on growth in the green sunfish, Lepomis cyanellus." Journal of Experimental Zoology 108.1 (1948): 1-19.
(Continued)

*Primary Examiner* — Chuong A Ngo
(74) *Attorney, Agent, or Firm* — NGUYEN TARBET IP LAW (57) ABSTRACT

Method and systems for measuring growth rate in plant or aquatic animal species such as embryonic or adult fish. The methods and systems utilize the measurement of $NADH_2$ production by detecting a colorimetric and fluorescent shift when a redox indicator such as resazurin is added to a sample. The colorimetric/fluorescent shift is indicative of the reduction of the redox indicator by $NADH_2$. The methods and systems of the present invention may be used to predict growth potential of a plant or animal, and measuring the growth rate of said plant or animal may be helpful for identifying and selecting individuals within a group that have greater growth potential. The methods and systems of the present invention may help eliminate the need for special equipment (e.g., for measuring oxygen consumption), decrease variability of measures, and minimize the effects of external factors (feeding/hormonal status).

11 Claims, 9 Drawing Sheets

Related U.S. Application Data (60) Provisional application No. 62/208,433, filed on Aug. 21, 2015.

(51) Int. Cl.
*C12Q 1/00* (2006.01)
*G01N 33/18* (2006.01)
*G01N 33/50* (2006.01)

(52) U.S. Cl.
CPC ..... *G01N 33/1806* (2013.01); *G01N 33/5005* (2013.01); *G01N 33/5088* (2013.01); *G01N 33/5097* (2013.01); *G01N 2333/43504* (2013.01); *G01N 2333/4603* (2013.01)

(58) Field of Classification Search
CPC . G01N 2333/43504; G01N 2333/4603; A01K 67/02; C12Q 1/008; Y02A 40/81
See application file for complete search history.

(56) References Cited

U.S. PATENT DOCUMENTS

| | | |
|---|---|---|
| 2007/0213399 A1 | 9/2007 | Messadek |
| 2008/0040044 A1 | 2/2008 | Dunlay et al. |
| 2008/0193966 A1* | 8/2008 | Steiner ............... G01N 33/52 435/32 |
| 2010/0197789 A1 | 8/2010 | Airma et al. |
| 2011/0321182 A1 | 12/2011 | Lehnert et al. |
| 2013/0251671 A1 | 9/2013 | Kaufman et al. |
| 2015/0344974 A1 | 12/2015 | Riggs et al. |

FOREIGN PATENT DOCUMENTS

| | | |
|---|---|---|
| WO | WO01/60152 A3 | 8/2001 |
| WO | WO0160152 A2 | 8/2001 |
| WO | 2008153632 A2 | 12/2008 |
| WO | WO2012167243 A1 | 12/2012 |
| WO | WO2017035064 A1 | 3/2017 |
| WO | WO2017187433 A1 | 11/2017 |
| WO | WO2018218161 A2 | 11/2018 |

OTHER PUBLICATIONS

Blanckenhorn, Wolf U. "Group size and the cost of agonistic behavior in pumpkinseed sunfish." Ethology ecology & evolution 4.3 (1992): 255-271.
Brand et al. "Evolution of energy metabolism. Proton permeability of the inner membrane of liver mitochondria is greater in a mammal than in a reptile." Biochemical Journal 275.1 (1991): 81-86.
Brown, Margaret E. "The growth of brown trout (Salmo trutta Linn.) I. Factors influencing the growth of trout fry." Journal of Experimental Biology 22.3-4 (1946): 118-129.
Clarke et al., "Scaling of metabolic rate with body mass and temperature in teleost fish." Journal of animal ecology 68.5 (1999): 893-905.
Conceição, L. E. C et al., "Cost of growth in larval and juvenile African catfish (Clarias gariepinus) in relation to growth rate, food intake and oxygen consumption." Aquaculture 161.1-4 (1998): 95-106.
Cook et al., "Effect of food deprivation on oxygen consumption and body composition of growth-enhanced transgenic Atlantic salmon (Salmo salar)." Aquaculture 188.1-2 (2000): 47-63.
Cutts et al. "Aggression and growth depression in juvenile Atlantic salmon: the consequences of individual variation in standard metabolic rate." Journal of Fish Biology 52.5 (1998): 1026-1037. entire document, especially abstract; p. 1027-1029 and p. 1035.
Gjedrem, T. "Genetic improvement of cold-water fish species." Aquaculture research 31.1 (2000): 25-33.
Gadagkar, Sudhindra R. "Social behaviour and growth rate variation in cultivated tilapia (Oreochromis niloticus)." (1997).

El-Greisy et al., "Monosex production of tilapia, Oreochromis niloticus using different doses of 17α-methyltestosterone with respect to the degree of sex stability after one year of treatment." The Egyptian Journal of Aquatic Research 38.1 (2012): 59-66.
Gjerde, Bjarne. "Growth and reproduction in fish and shellfish." Aquaculture 57.1-4 (1986): 37-55.
Grant, "Aggressiveness and the Foraging Behavior of Yung-of-the-Year Brook Charr (Salvelinus fontinalis)" Canadian Journal of Fisheries and Aquatic Sciences, 1990. 47(5): p. 915-920.
Green B.S., Maternal Effects in Fish Populations, Advances in Marine Biology, vol. 54 (2008).
Heath et al., Maternal Effects on Offspring Size: Variation Through Early Development of Chinook Salmon Evolution, vol. 53, No. 5 (Oct. 1999), pp. 1605-1611.
Huang et al., "Response to mass selection for growth rate in Oreochromis niloticus." Aquaculture 85.1-4 (1990): 199-205.
Hulata et al., "Mass selection for growth rate in the Nile tilapia (Oreochromis niloticus)." Aquaculture 57.1-4 (1986): 177-184.
Huntingford, F. A., et al. "Social dominance and body size in Atlantic salmon parr, Salmo solar L." Journal of Fish Biology 36.6 (1990): 877-881.
Koebele, Bruce P. "Growth and the size hierarchy effect: an experimental assessment of three proposed mechanisms; activity differences, disproportional food acquisition, physiological stress." Environmental Biology of Fishes 12.3 (1985): 181-188.
Livingston, Robert J. "A volumetric respirometer for long-term studies of small aquatic animals." Journal of the Marine Biological Association of the United Kingdom 48.2 (1968): 485-497.
Magnuson, John J. "An analysis of aggressive behavior, growth, and competition for food and space in medaka (Oryzias latipes (Pisces, Cyprinodontidae))." Canadian Journal of Zoology 40.2 (1962): 313-363.
Mauger et al., "Cryobanking of fish somatic cells: optimizations of fin explant culture and fin cell cryopreservation." Comparative Biochemistry and Physiology Part B: Biochemistry and Molecular Biology 144.1 (2006): 29-37.
McCarthy et al., "The effect of feeding hierarchy on individual variability in daily feeding of rainbow trout, Oncorhynchus mykiss (Walbaum)." Journal of Fish Biology 41.2 (1992): 257-263.
Miyashima, et al. "Relationship between oxygen consumption, growth and survival of larval fish." Aquaculture Research 43.5 (2012): 679-687.
Palada-De Vera, M.S. and A.E. Eknath. Predictability of individual growth rates in tilapia. in Proceedings of the fourth International Symposium on Genetics in Aquaculture. 1993. Wuhan, Hubei Province, China: Elsevier.
Purdom "Variation in Fish" in Sea Fisheries Research, F.R.H. Jones, Editor. 1974, Elek Science: London. p. 347-355.
Rampersad et al. "Multiple applications of Alamar Blue as an indicator of metabolic function and cellular health in cell viability bioassays." Sensors 12.9 (2012): 12347-12360. entire document, especially abstract; p. 12350, p. 12351 and p. 12354.
Renquist et al. "Development of an assay for high-throughput energy expenditure monitoring in the zebrafish." Zebrafish 10.3 (2013): 343-352.
Seiler et al., "A comparison of aggressive and foraging behaviour between juvenile cutthroat trout, rainbow trout and F1 hybrids." Animal Behaviour 74.6 (2007): 1805-1812.
Smith et al., "Protein synthesis and oxygen consumption in fish cells." Journal of Comparative Physiology B 165.2 (1995): 93-101.
Tave et al., "Predicted response to selection for early growth in Tilapia nilotica." Transactions of the American Fisheries Society 109.4 (1980): 439-445.
Thodesen et al. "Genetic improvement of tilapias in China: genetic parameters and selection responses in growth of Nile tilapia (Oreochromis niloticus) after six generations of multi-trait selection for growth and fillet yield." Aquaculture 322 (2011): 51-64.
Van Meter, David E. "Needle biopsy procedure for electrophoresis in fishes." The Progressive Fish-Culturist 57.2 (1995): 166-167.
Williams, S.Y. and B.J. Renquist, High Throughput Danio Rerio Energy Expenditure Assay. Journal of Visualized Experiments, Issue 107, https://www.jove.com/video/53297, Jan. 2016.
Wohlfarth, G. W. "Shoot carp." Bamidgeh 29.2 (1977): 35-56.

(56) References Cited

OTHER PUBLICATIONS

Liu et al. Combination of Entner-Doudoroff Pathway With MEP Increases Isoprene Production in Engineered *Escherichia coli*, PLoS One, 2013, vol. 8, No. 12, e83290, pp. 1-7.
International Search Report Issued for PCT Application No. PCT/US18/61349 on Jan. 29, 2019.
European Search Report issued for EP Application No. 16839933.5 on Dec. 5, 2018.
Jordan Rosenfeld et al: "Relationship between growth and standard metabolic rate measurement artefacts and Implications for habitat use and life-history adaptation in salmonids", Journal of Animal Ecology, vol. 84, No. 1, Aug. 4, 2014, pp. 4-20.
Donald Reid et al: "The performance advantage of a high resting metabolic rate in juvenile salmon is habitat dependent: RMR, dominance, habitat and growth in salmon", Journal of Animal Ecology, vol. 81, No. 4, Jul. 1, 2012, pp. 868-875.
Tian J. et al., Oral Treatment with gamma-Aminobutyric Acid Improves Glucose Tolerance and Insulin Sensitivity by Inhibiting Inflammation in High Fat Diet-Fed Mice, PLOS One, Sep. 22, 2011, vol. 29, issue 24, United States of America.
Coscina et al. GABA and feeding: Reversal of overeating by central GABA-transaminase inhibition11, Progress in Neuro-Psychopharmacology & Biological Psychiatry, Elsevier, GB, vol. 7, No. 4-6, Jan. 1, 1983 (Jan. 1, 1983).
Rotiroti D et al: Evidence that a GABAergic mechanism influences the development of DOCA-salt hypertension In the rat11, European Journal of Pharmacology, Elsevier Science, NL, vol. 83, No. 1-2, Sep. 10, 1982 (Sep. 10, 1982).
Squadrito F et al: A Decreased Brainstem Content of Gaba Mediates Hyperinsulinemia in Obese Zucker RATS11, Neuroscience Research Communications, Wiley, Chichester, GB, vol. 8, No. 1, Jan. 1, 1991 (Jan. 1, 1991).
Kathirvel Elango et al: Betaine improves nonalcoholic fatty liver and associated hepatic insulin resistance: a potential mechanism for hepatoprotection by betaine, American Journal of Physiology—Gastrointestinal and Liver Physiology, vol. 299, No. 5, Nov. 1, 2010 (Nov. 1, 2010).
Renquist B: "Progress Report: Metabolic Rate Assay to Predict Growth Rate of Aquaculture Species 1 Part I: Project Title: Efficient, Rapid Assay for Predicting the Growth Rate of Aquaculture Species Based on Metabolic Rate of the Fertilized Egg Report Given in Year 2014", Jan. 1, 2014 (Jan. 1, 2014).
Minuk G. Y., Gamma-aminobutyric-acid and the liver, Digestive Diseases, Feb. 1993, pp. 45-54, vol. 11, Canada.
Borra et al. "A simple method to measure cell viability in proliferation and cytotoxicity assays." Brazilian oral research 23.3 (2009): 255-262.
Cooper et al. "Anorexic effects of ethanolamine-O-sulfate and muscimol in the rat: evidence that GABA inhibits Ingestive behavior." Life sciences 26.23 (1980): 1997-2002.
Holst, C. Martina, and Stina M. Oredsson. "Comparison of three cytotoxicity tests in the evaluation of the cytotoxicity of a spermine analogue on human breast cancer cell lines." Toxicology in vitro 19.3 (2005): 379-387.

\* cited by examiner

| Well (Figure 1) | Visual Rank | R | G | B |
|---|---|---|---|---|
| G3 | 1 | 161 | 77 | 105 |
| G9 | 2 | 144 | 113 | 172 |
| G5 | 3 | 129 | 132 | 175 |
| G4 | 4 | 105 | 112 | 161 |
| G6 | 5 | 100 | 116 | 165 |
| G8 | 6 | 89 | 104 | 144 |
| G7 | 7 | 79 | 93 | 134 |
| G10 | 8 | 79 | 93 | 122 |

METHODS AND SYSTEMS FOR MEASURING GROWTH RATE IN PLANT OR AQUATIC ANIMAL SPECIES

CROSS REFERENCE

This application is a Divisional and claims benefit of U.S. patent application Ser. No. 15/754,126 filed Feb. 21, 2018, which is a 371 application and claims benefit of PCT Application No. PCT/US16/48006 filed Aug. 22, 2016, which claims benefit of U.S. Provisional Patent Application No. 62/208,433 filed Aug. 21, 2015, the specification(s) of which is/are incorporated herein in their entirety by reference.

GOVERNMENT SUPPORT

This invention was made with government support under Grant No. 2010-38500-21758 awarded by USDA/NIFA. The government has certain rights in the invention.

FIELD OF THE INVENTION

The present invention relates to methods for measuring metabolic rate in cells, more particularly to methods for measuring $NADH_2$ concentrations and production in cells, more particularly to measuring $NAHD_2$ concentrations and production in cells of plants and/or aquatic animals for predicting growth potential of said plants and animals.

BACKGROUND OF THE INVENTION

In fish species, growth is positively correlated with energy expenditure. Current methods of measuring metabolic rate in fish species involve measuring oxygen consumption, e.g., measuring oxygen consumption per unit of body weight. However, measuring oxygen consumption requires specialized equipment, training so as to limit fish stress, and an understanding of factors that influence metabolic rate (e.g., feeding status, hormonal status).

The present invention features methods and systems (e.g., a colorimetric/fluorescent methods and systems) for measuring metabolic rate in plants or aquatic animal species (e.g., embryonic fish, zebrafish, tilapia, trout, etc.). For example, the present invention features measuring over a period of time (e.g., 1 to 72 hours) the production of $NADH_2$, which is a product of metabolism and thus a direct indicator of the flux of metabolites through metabolite oxidation. The methods and systems of the present invention may monitor $NADH_2$ using a redox indicator (e.g., resazurin/resorufin or other appropriate indicator (e.g., $NADH_2$ indicator) such as but not limited to tetrazolium dyes, e.g., MTT, XTT, MTS, WST). The redox indicator is reduced by $NADH_2$, resulting in a colorimetric and fluorescent shift in solution. In some embodiments, the redox indicator remains reduced, and therefore can be used to provide a cumulative measurement of energy expenditure over a time period.

A review of maternal effects in fish populations (Green, 2008, Advances in Marine Biology 54:1-105) discusses that female identity explained a large proportion of variation in egg diameter and in hatching length (e.g., the size of the mother could largely predict the size of the hatchling). Heath and colleagues (Heath et al., 1999, Evolution 53(5):1605-1611) studied the maternal effect on progeny growth and found that by 180 days, there was no detectable difference between the progeny that were initially bigger due to maternal effect and the progeny that were not. Thus, using size and weights of females, embryos, or hatchlings, one cannot necessarily predict how large fish will be beyond the maternal affect time period (e.g., 2 months). It was surprisingly discovered that measuring metabolic rate allowed for the prediction of growth potential beyond the time frame associated with the maternal effect (e.g., to harvest size), and that high metabolic rates were indicative of high growth potential. Further, in warm-blooded animals, high metabolic rates are associated with slower growth. It was surprisingly discovered that in fish, high metabolic rates are associated with high growth. In oysters, inbred, slow growing lines have a higher metabolic rate than outcrossed fast growing families.

The methods and systems of the present invention may be used to assess the genetic potential for growth of the plant or animal. For example, the methods and systems may be used to predict the growth potential of a plant or animal. Measuring the metabolic rate of said plant or animal may be helpful for identifying and selecting individuals within a group that have greater predicted growth potential, e.g., individuals that are most likely to grow faster and/or larger. For example, fish with a high metabolic rate as embryos may weigh more than 30% more at eight months as compared to fish that have low metabolic rates as embryos. The methods and systems of the present invention may also be used to segregate fast and slow growing fish. These applications may be beneficial for the aquaculture industry, e.g., hatcheries, fish farms or the like. For example, without wishing to limit the present invention to any theory or mechanism, it is believed that the methods and systems of the present invention, which may allow for selection of genetically superior brood stock, may have a positive impact on profitability given that selecting for genetic potential for growth currently has been limited by (a) interactions between aggression and growth, (b) inability to select in wild-caught brood stock, and (c) the long generation interval in slow maturing species.

Without wishing to limit the present invention to any theory or mechanism, it is believed that the methods and systems of the present invention may help eliminate the need for special equipment (e.g., for measuring oxygen consumption), decrease variability of measures, and minimize the effects of external factors (feeding/hormonal status).

The present invention is not limited to use in aquatic animal species (e.g., embryonic fish, zebrafish, tilapia, trout, etc., with the ability to work with tissue explants and/or primary cells).

The present invention may also be used in plants. For example, the present invention may be used to test soil, water, and/or fertilizers. In some embodiments, the plants with the best genetics for growth may be selected. In some embodiments, water quality or soil quality is assessed. In some embodiments, the ability of different fertilizers to enhance growth is assessed.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The present invention features a method of brood stock separation from a pool of individuals (fish, other aquatic organisms, cells or plants). In some embodiments, the method comprises measuring whole body metabolic rate in embryonic or juvenile organisms, wherein metabolic rate is measured using a colorimetric/fluorescent redox assay comprising introducing a redox indicator to the cell sample at time $T_0$, measuring a fluorescence value at time $T_0$, and measuring a fluorescence value at time $T_1$ after time $T_0$; and determining the change in fluorescence between $T_1$ and $T_0$ to determine a metabolic rate. In some embodiments the method comprises measuring metabolic rate a tissue sample, wherein metabolic rate is measured using a colorimetric/fluorescent redox assay comprising introducing a redox indicator to the cell sample at time $T_0$, measuring a fluorescence value at time $T_0$, and measuring a fluorescence value at time $T_1$ after time $T_0$; and determining the change in fluorescence between $T_1$ and $T_0$ to determine a metabolic rate. The method comprises separating the fish or plants based on metabolic rate.

The present invention also features a method of brood stock separation from a pool of individuals. In some embodiments, the method comprises measuring whole body metabolic rate in a cell sample from each individual, wherein metabolic rate is measured using a colorimetric/fluorescent redox assay comprising introducing a redox indicator to the cell sample at time $T_0$; measuring a fluorescence value at time $T_0$; measuring a fluorescence value at time $T_1$ after time $T_0$; and determining the change in fluorescence between $T_1$ and $T_0$ to determine a metabolic rate; and separating the individuals in the group that had a metabolic rate in the 10% highest metabolic rates of the group from the remaining individuals in the group. In some embodiments, the pool of individuals comprises embryonic or juvenile aquatic organisms, cells, or plants. In some embodiments, the aquatic organisms are fish embryos. In some embodiments, the aquatic organisms are adult fish. In some embodiments, the individuals in the group that had a metabolic rate in the 5% highest metabolic rates of the group are separated from the remaining individuals in the group.

The present invention also features a method of stock separation of a pool of fish or a group of plants, wherein a tissue sample is obtained from each fish of the pool or each plant in the group. In some embodiments, the method comprises measuring metabolic rate in each tissue sample, wherein metabolic rate is measured using a colorimetric/fluorescent redox assay comprising introducing a redox indicator to the cell sample at time $T_0$, measuring a fluorescence value at time $T_0$, and measuring a fluorescence value at time $T_1$ after time $T_0$; and determining the change in fluorescence between $T_1$ and $T_0$ to determine a metabolic rate; and separating the fish or plants that had a metabolic rate that is in the 10% highest metabolic rates of the pool of fish or group of plants from the remaining fish or plants.

In some embodiments, the fish are fish embryos. In some embodiments, the fish are adult fish. In some embodiments, the sample comprises a tissue explant. In some embodiments, the fish that are in the 5% highest metabolic rates are separated from the remaining fish. In some embodiments, the redox indicator comprises AlamarBlue®, resazurin, a tetrazolium dye, or PrestoBlue®. In some embodiments, $T_1$ is equal to $T_0$ plus 8 hours. In some embodiments, $T_1$ is equal to $T_0$ plus 16 hours. In some embodiments, $T_1$ is equal to $T_0$ plus 24 hours. In some embodiments, measuring a fluorescence value comprises using a fluorescent plate reader. In some embodiments, measuring a fluorescence value comprises obtaining a digital photograph of the cell sample and quantitating red, green, and blue color intensity, wherein the intensities are correlated with fluorescence to determine a quantitative measurement of metabolic rate.

The present invention also features a method for predicting growth of individual organisms within a group. In some embodiments, the method comprises measuring metabolic rate in a cell sample of the organism by performing a colorimetric/fluorescent redox assay comprising introducing a redox indicator to the cell sample at time $T_0$, measuring a fluorescence value at time $T_0$, and measuring a fluorescence value at time $T_1$; determining a metabolic rate by calculating the change in fluorescence between $T_1$ and $T_0$; and comparing the metabolic rates of each of the organisms within the group; wherein a first organism with a higher metabolic rate than a second organism will be bigger, heavier, or both bigger and heavier at a time beyond a time associated with material effect.

In some embodiments, the organism is a plant or aquatic animal. In some embodiments, the aquatic animal is a fish. In some embodiments, the organism is an embryonic aquatic organism. In some embodiments, the organism is an adult aquatic organism. In some embodiments, the redox indicator comprises AlamarBlue®, resazurin, a tetrazolium dye, or PrestoBlue®. In some embodiments, $T_1$ is equal to $T_0$ plus any given duration of time. In some embodiments, $T_1$ is equal to $T_0$ plus 16 hours. In some embodiments, $T_1$ is equal to $T_0$ plus 24 hours. In some embodiments, measuring a fluorescence or absorbance value is assessed using a spectrophotometer with or without fluorescent capabilities. In some embodiments, measuring a fluorescence value comprises obtaining a digital photograph of the cell sample and quantitating red, green, and blue color intensity, wherein the intensities are correlated with fluorescence to determine a quantitative measurement of metabolic rate. In some embodiments, the time beyond the time associated with maternal effect is harvest time. In some embodiments, the time beyond the time associated with maternal effect is 3 months. In some embodiments, the time beyond the time associated with maternal effect is 8 months.

The present invention also features a method for assessing genetic potential for growth of individual organisms within a group. In some embodiments, the method comprises measuring metabolic rate in a cell sample of each of the organism by performing a colorimetric/fluorescent redox assay comprising introducing a redox indicator to the cell sample at time $T_0$, measuring a fluorescence value at time $T_0$, and measuring a fluorescence value at time determining a metabolic rate by calculating the change in fluorescence between $T_1$ and $T_0$; and comparing the metabolic rates of each of the organisms within the group; wherein a first organism with a higher metabolic rate than a second organism has a higher potential for growth than does the second organism.

In some embodiments, the redox indicator comprises AlamarBlue®, resazurin, a tetrazolium dye, or PrestoBlue®. In some embodiments, $T_1$ is equal to $T_0$ plus 8 hours. In some embodiments, $T_1$ is equal to $T_0$ plus 16 hours. In some embodiments, $T_1$ is equal to $T_0$ plus 24 hours. In some embodiments, measuring a fluorescence value comprises using a fluorescent plate reader. In some embodiments, measuring a fluorescence value comprises obtaining a digital photograph of the cell sample and quantitating red, green, and blue color intensity, wherein the intensities are correlated with fluorescence to determine a quantitative measurement of metabolic rate.

BRIEF DESCRIPTION OF THE DRAWINGS

The features and advantages of the present invention will become apparent from a consideration of the following detailed description presented in connection with the accompanying drawings in which:

FIG. 4A-4B relate to isolated cells from skeletal muscle and fin cell explants.

FIG. 10A-10B show representative results from Oyster Spat.

FIG. 13A-13D show changes in fluorescence with various numbers of tilapia (FIG. 13A), trout (FIG. 13B), oysters (FIG. 13C), and shrimp (FIG. 13D) in a set volume. FIG. 13A-13D show that metabolic rate within a well (given volume) increases as the number of individuals within that well (volume) increases.

DETAILED DESCRIPTION OF THE INVENTION

The present invention features methods and for measuring growth rate in plant or aquatic animal species. The methods and systems of the present invention may be used to predict growth potential of a plant or animal, and measuring the growth rate of said plant or animal may be helpful for identifying and selecting individuals within a group that have greater growth potential, e.g., individuals that are most likely to grow faster and/or larger.

The methods for measuring growth rate (and/or for predicting growth potential) comprise measuring (over a period of time) the production of $NADH_2$ using a redox indicator (e.g., resazurin/resorufin or other appropriate indicator). The redox indicator is reduced by $NADH_2$, resulting in a colorimetric and fluorescent shift in solution (e.g., using AlamarBlue® reduction, pink, purple and blue wells may be indicative of embryos with high, moderate, and low metabolic rates, respectively). The redox indicator remains reduced, and therefore can be used to provide a cumulative measurement of energy expenditure over a time period. Redox indicators may include but are not limited to resazurin, a tetrazolium dye (e.g., MTT, XTT, MTS, WST), PrestoBlue®, or any other appropriate $NADH_2$ production indicator.

Figure 1:
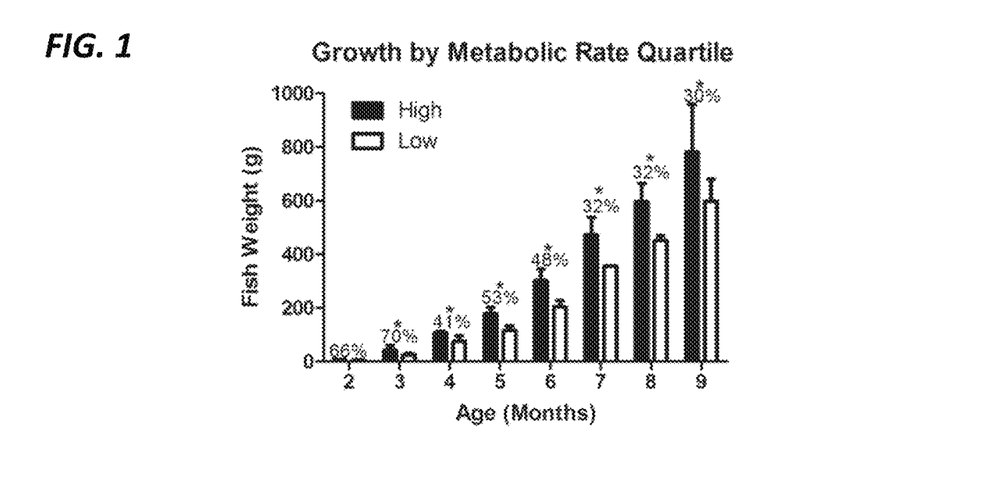
FIG. 1 shows growth rates of embryos segregated into high and low metabolic rate quartiles. *P<0.05.

FIG. 1 shows that embryonic fish metabolic rate may be used to predict future growth. As used herein, the term "fish embryo" and "embryonic fish" may be used interchangeably, referring to a fish in an embryonic stage, e.g., not yet feeding, relying on yolk for nutrients. Further, if fish (e.g., tilapia) are segregated by metabolic rate, fish with a metabolic rate in the highest quartile grow faster than fish with a metabolic rate in the lowest quartile. FIG. 1 also suggests that high metabolic rate fish maintain a growth advantage for at least 8 months. In some embodiments, the present invention can be used to predict growth at 3 months, 4 months, 5 months, 6 months, 7 months, 8 months, 9 months, etc. In some embodiments, the present invention can be used to predict growth of the animal, e.g., fish, at harvest size/time. In some embodiments, the present invention can be used to predict growth of the animal, e.g., fish, at a time after the maternal effect time period has passed.

Figure 2:
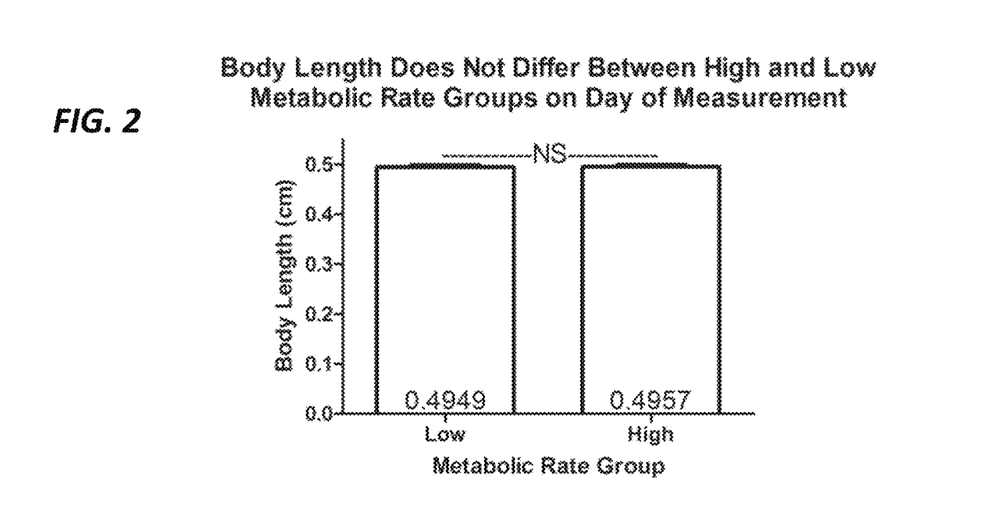
FIG. 2 shows body length vs. metabolic rate. Body length is similar in high and low metabolic rate embryonic fish on the day the assay is performed.

Regarding FIG. 1, studies on growth were conducted in three cohorts of high and low metabolic rate fish (n=3). Each cohort included measurement of metabolic rate in at least 6,000 embryonic fish so that each metabolic rate group included 1500 fish/experimental unit (n). Because these fish were fed identically, this increased growth is also indicative of improved feed conversion. Importantly, body length of these embryonic fish does not differ on the day and time that the AlamarBlue assay was completed (see FIG. 2). Thus, fish that are larger at the time were not selected for when the assay was performed.

An example of a method for measuring metabolic rate (e.g., metabolic rate assay) is as follows: Embryonic tilapia are rinsed 3 times in sterile 28° C. fish water. Using a disposable plastic pipette, embryonic fish are individually transferred into wells of a 96-well plate. Once plated, 96-well plates containing fish are put into an incubator to maintain a water temperature of 28° C. Upon completion of plating, all water is removed from the well and is replaced with 300 µl sterile filtered assay medium (Fish system water including, 4 mM $NaHCO_3$, 0.1% DMSO, and 0.16% AlamarBlue (Cat. #Y00010; Thermo Fisher Scientific Inc.; Waltham, MA)). Fluorescence is determined using a fluorescent plate reader (excitation wavelength 530 and emission wavelength 590) at the beginning of the assay to establish a baseline for each embryo and at the end of the assay (e.g., at 16 h). A large change in fluorescence is indicative of robust $NADH_2$ production and a high metabolic rate, while a small change in fluorescence is indicative of a low metabolic rate.

The methods and systems of the present invention are not limited to the aforementioned example. Note that it may be possible for a single investigator to perform the metabolic rate assay on approximately 2,500 embryonic fish/8 hr day.

Figure 3A:
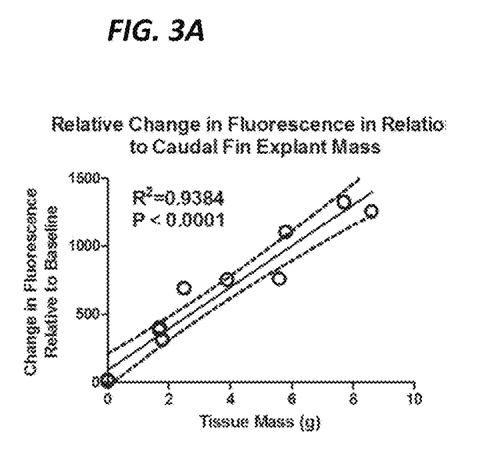
FIG. 3A-3D show that changes in fluorescence is highly correlated with caudal fin (FIG. 3A) and skeletal muscle (FIG. 3B) explant mass. Changes in fluorescence increase with duration of incubation with caudal fin (FIG. 3C) and skeletal muscle (FIG. 3D) explants.
Figure 3B:
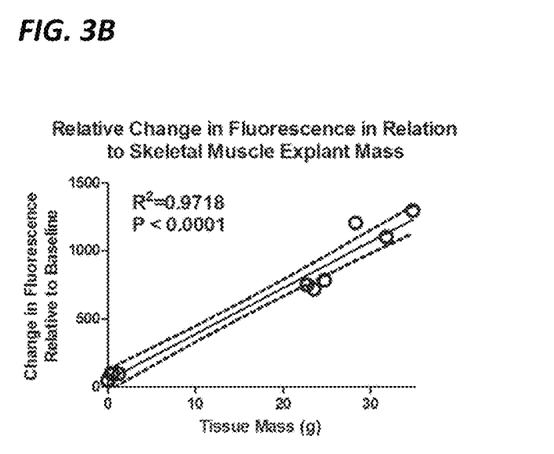
Figure 3C:
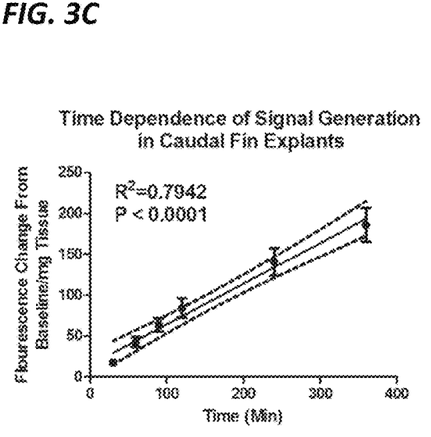
Figure 3D:
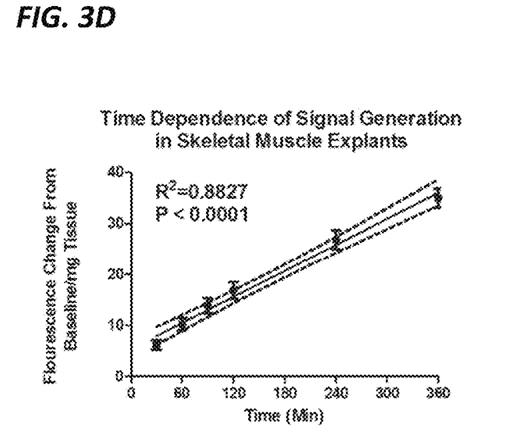

Although selection of brood stock as embryos may work well in captive bred fish with short generation intervals, application in either wild caught brood stock or slow maturing fish species requires the ability to assess the genetic potential for growth of adult fish. Preliminary studies establish that the methods and systems of the present invention (e.g., redox assay using AlamarBlue) may be used to assess the metabolic rate of skeletal muscle or caudal fin clip explants. FIG. 3A and FIG. 3B shows that within samples collected from the same fish, the change in fluorescence is directly related to the size of the fin or skeletal muscle explant. Moreover, like previously observed in embryonic fish, explants increase the signal generated with time (see FIG. 3C, FIG. 3D).

Figure 4A:
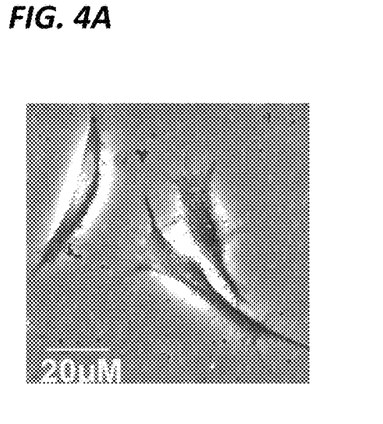
FIG. 4A: Skeletal muscle satellite cells differentiate into proliferating myoblasts.
Figure 4B:
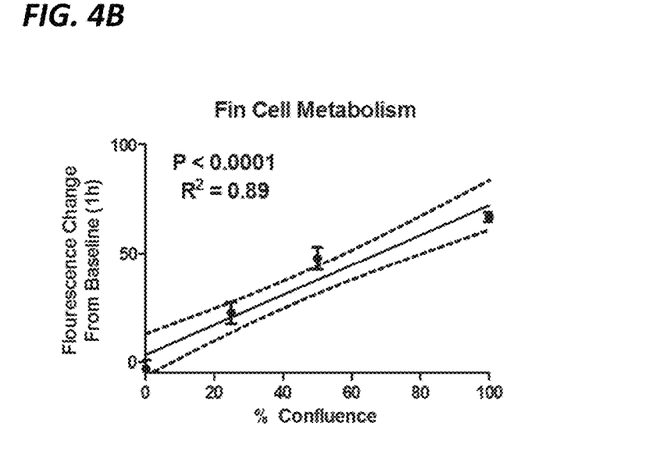
FIG. 4B: Using caudal fin derived cells, the percent confluence was varied to create a range of total metabolic rates within a well. Fluorescent change from baseline, increased with # of fin cells in a well (P<0.0001).

Epithelial cells from fin explants and satellite cells from skeletal muscle have been isolated. FIG. 4A shows the satellite cells from skeletal muscle can differentiate into proliferating myoblasts. FIG. 4B shows that AlamarBlue can measure changes in fish fin cell density within a well. Without wishing to limit the present invention to any theory or mechanism, it is believed that in vitro metabolic rate of skeletal muscle satellite cell derived myoblasts and caudal fin epithelial cells expressed as change in fluorescence per µg DNA may help segregate fish with high and low metabolic rates.

As previously discussed, the present invention features methods for predicting growth in an organism (e.g., a plant, aquatic animal, e.g., fish, embryonic fish, adult fish, etc.). In some embodiments, the method comprising measuring the metabolic rate in a cell sample of the organism. This may be done by performing a colorimetric/fluorescent redox assay comprising introducing a redox indicator (e.g., resazurin) to the cell sample at time $T_0$, measuring a fluorescence value at time $T_0$, and measuring a fluorescence value at time $T_1$. The change in fluorescence between $T_1$ and $T_0$ can be calculated to determine the metabolic rate. A high metabolic rate is indicative of a high growth rate, and a low metabolic rate is indicative of a low growth rate.

The redox assay may be performed over a period of time such as 2 hours, 4 hours, 6 hours, 8 hours, 10 hours, 12 hours, 14 hours, 16 hours, 20 hours, 24 hours, etc. As such, in some embodiments, $T_1$ is equal to $T_0$ plus 8 hours, $T_0$ plus 16 hours, $T_0$ plus 24 hours, etc. The present invention is not limited to these times.

Fluorescence may be determined in a variety of ways. For example, in some embodiments, fluorescence is calculated using a fluorescent plate reader. In some embodiments, absorbance/fluorescence is calculated using a digital photograph of the cell sample. In some embodiments, the red, green, and blue color intensity is quantitated. The intensities may be correlated with fluorescence to determine a quantitative measurement of metabolic rate.

The present invention also features a method for brood stock selection. A sample (e.g., cell sample) may be obtained from each fish (e.g., fish embryos, adult fish, etc.). In some embodiments, the method comprises measuring the metabolic rate in each tissue sample and comparing the metabolic rates of each fish in the pool. Particular fish may be selected based on their metabolic rate. For example, in some embodiments, fish that have a metabolic rate that is in the top 50%, top 40%, top 30%, top 20%, top 10%, etc. may be selected.

Figure 5:
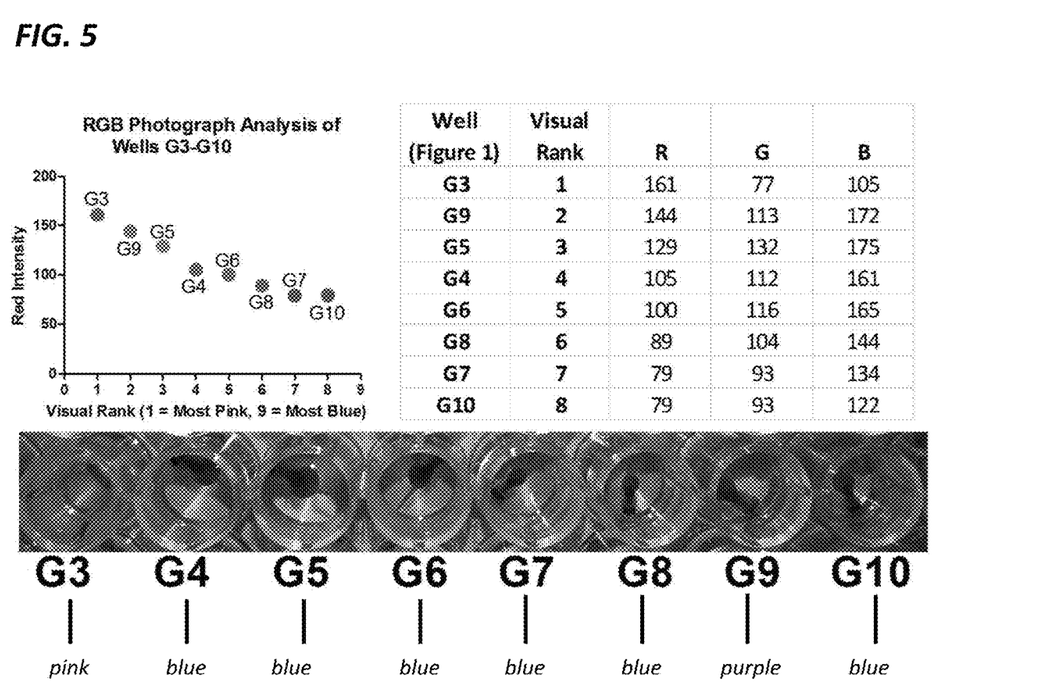
FIG. 5 shows an analysis of RGB spectrum from wells (G3-G10) in an experiment using AlamarBlue® reduction methods (pink, purple and blue wells were indicative of embryos with high, moderate, and low metabolic rates, respectively.) Care was taken to ensure measurement was taken neither in a shadow nor ray of light. This preliminary analysis suggests that digital photograph analysis of red spectrum intensity can be used to quantitatively sort wells based on color change. Colors of dots for each well represent the exact RGB spectrum from the analysis.

The present invention also features selection based on metabolic rate through computer aided red-green-blue (RGB) analysis of digital photographs (see FIG. 5.)

Because selection for the genetic potential for growth has been limited by 1) interactions between aggression and growth, 2) inability to select in wild-caught brood stock, and 3) the long generation interval in slow maturing species, the methods of the present invention may allow for selection of genetically superior brood stock, which may have a positive impact on profitability of the aquaculturalist. FIG. 5 shows that metabolic rate has a distribution with a right extending tail; thus, it may be possible to impose a large selection differential to maximize the response to selection based on metabolic rate. In those industries that are dependent on wild caught brood stock, the methods of the present invention may be used first to allow for selection. In late maturing species (e.g., sturgeon), by increasing growth it may be possible to shorten the duration to maturation.

Figure 6:
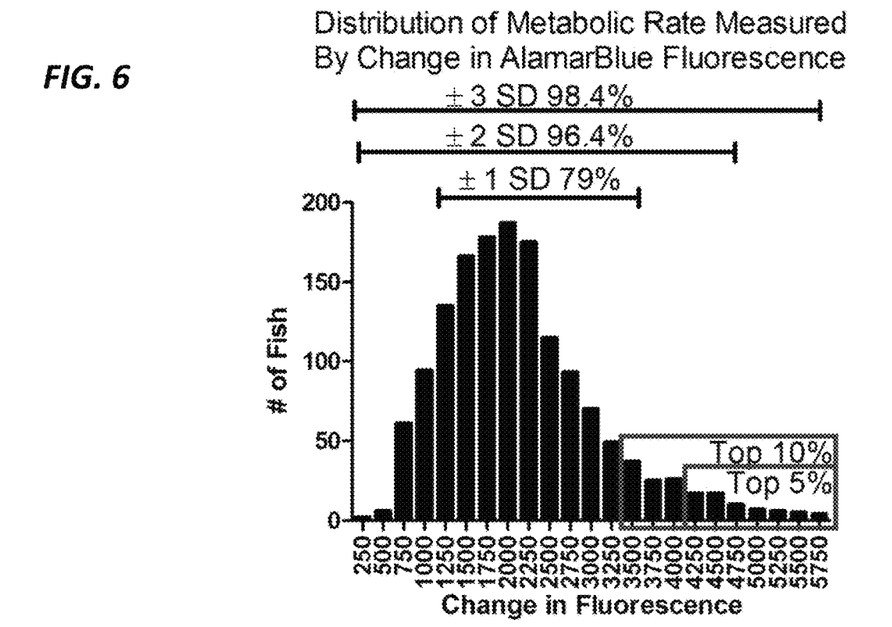
FIG. 6 shows a histogram displaying the frequency distribution of metabolic rates measured by change in fluorescence. Note the long right tail composed of fish that have a high selective differential from the mean.
Figure 7:
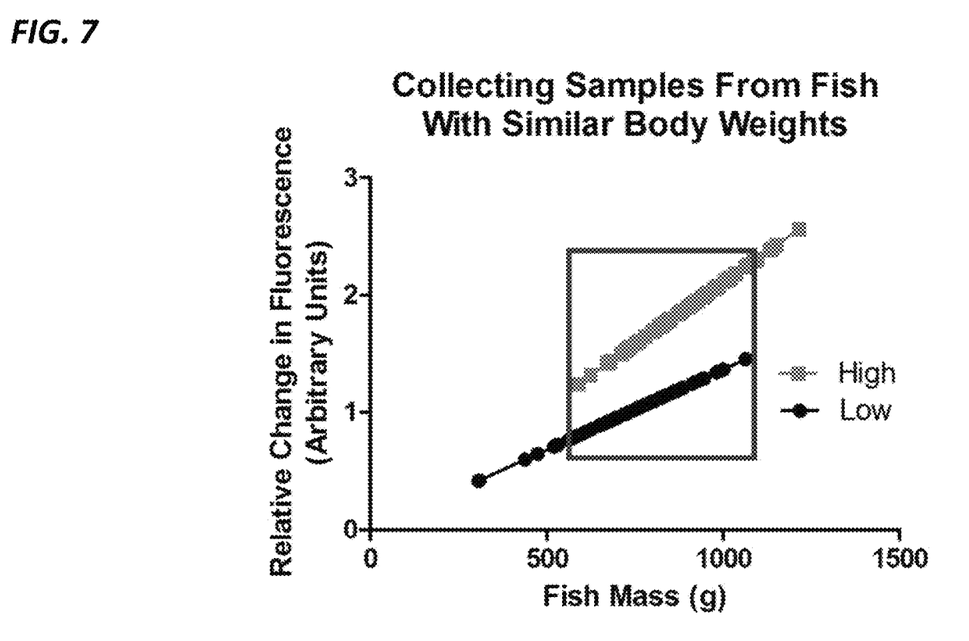
FIG. 7 shows comparisons between high and low metabolic rate fish made at identical weights. Slope within metabolic rate group will determine the relationship between current body weight and explant metabolic rate. Body weight data is from fish that are already selected; thus, selection of fish with similar masses in each group may be feasible.
Figure 8A:
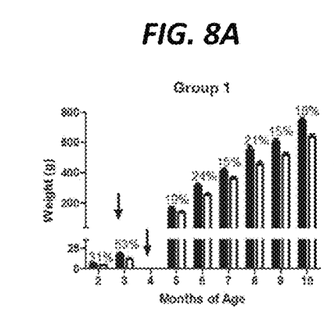
FIG. 8A-8C show the growth advantage in tilapia that had a high metabolic rate (top quartile) as embryos relative to those embryos that have a low metabolic rate (bottom quartile). The percent increase in growth attributable to the high metabolic rate is show at each time point for each group (FIG. 8A is group 1, FIG. 8B is group 2, and FIG. 8C is group 3). At all time points significant differences existed.
Figure 8B:
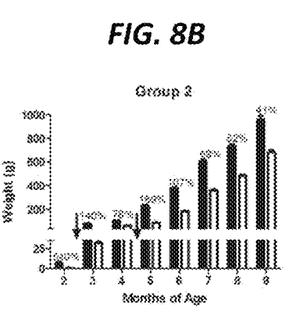
Figure 8C:
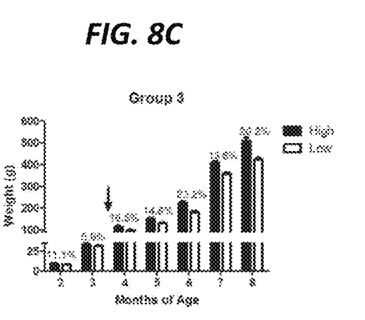

FIG. 6 shows a histogram displaying the frequency distribution of metabolic rates measured by change in fluorescence. Note the long right tail composed of fish that have a high selective differential from the mean. FIG. 7 shows comparisons between high and low metabolic rate fish made at identical weights. Slope within metabolic rate group will determine the relationship between current body weight and explant metabolic rate. Body weight data is from fish that are already selected; thus, selection of fish with similar masses in each group may be feasible. FIG. 8A-8C show the growth advantage in tilapia that had a high metabolic rate (top quartile) as embryos relative to those embryos that have a low metabolic rate (bottom quartile). The percent increase in growth attributable to the high metabolic rate is show at each time point for each group. At all time points significant differences existed.

Figure 9A:
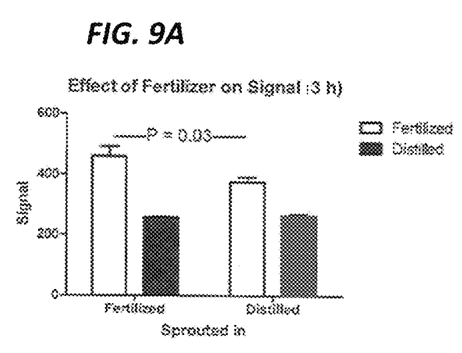
FIG. 9A-9C show AlamarBlue reduction results in lettuce seeds. Lettuce seeds were sprouted in either fertilized or distilled water then transferred to either fertilized or distilled water 3 days later for analysis of AlamarBlue reduction. Plants placed into fertilized water showed increased AlmarBlue reduction at both 3 hours (FIG. 9A) and 24 hours (FIG. 9B) relative to plants that were placed into distilled water. Of note those plants that were sprouted in distilled water did generate significantly less signal in fertilized water during the first 3 hours of incubation than lettuce sprouts that were always in fertilized water. Also shown in FIG. 9C is signal increase with duration of exposure of the lettuce sprout to AlamarBlue, which is an indication of the cumulative nature of this assay. This figure suggests that this assay can be used to test the nutrient quality of water or soil.
Figure 9B:
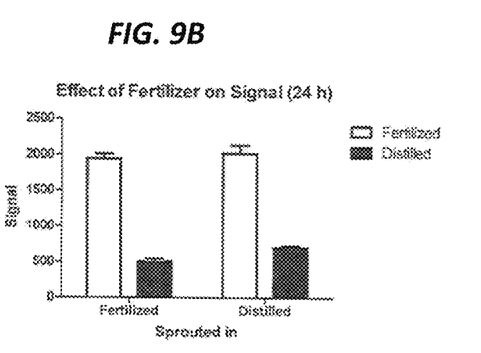
Figure 9C:
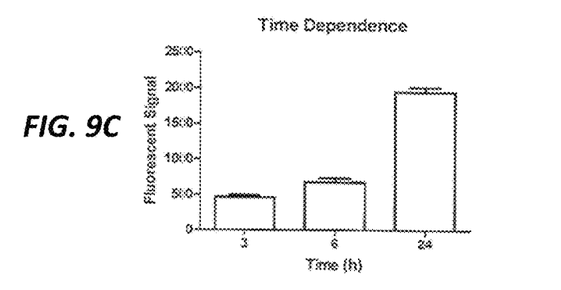

As previously discussed and as shown in FIG. 9A-9C, the present invention may also be used in plants. For example, the present invention may be used to test soil, water, and/or fertilizers. In some embodiments, the plants with the best genetics for growth may be selected. In some embodiments, water quality or soil quality is assessed. In some embodiments, the ability of different fertilizers to enhance growth is assessed.

Example 1: Monitoring $NADH_2$ Production by Adult Cells

Example 1 is an example of the use of the methods and systems of the present invention. The present invention is not limited to the examples set forth in Example 1.

Example 1 describes assessing metabolic rate in adult fish, e.g., assessing the metabolic rate of tissue explants/cells collected from adult fish that were segregated by metabolic rate as embryos. This may be used as a means of selecting for captive bred species. For example, the present invention may be used to assess the ability to ascertain genetic potential for growth of adult fish by measuring metabolic rate using minimally invasive, non-lethal techniques to collect fin and skeletal muscle samples. Without wishing to limit the present invention to any theory or mechanism, it is believed that the methods and systems of the present invention may be used to evaluate wild caught and slow maturing brood stock. For example, it is believed that adult cells/explants from fish that had a high metabolic rate as embryos will have a higher ex vivo metabolic rate than cells/explant from tilapia that had a low metabolic rate as embryos.

Fin Sampling: Fish will be weighed then anesthetized in a solution of tricaine methane sulfonate (MS222, 100 mg/L). Mucus will be wiped from the caudal fin. Sterile scissors or a tissue punch will be used to remove a piece of fin ray from between the bones of the caudal fin. Bacterial contamination will be limited by rinsing 3 times for 5 minutes in L-15 media with Gentamycin (100 μg/ml), and fungizone (2.5 μg/ml).

Explant metabolic rate: Tissue is plated in 300 μl assay media (L-15 media without phenol red supplemented with 25 mM HEPES, 5 mM $NaHCO_3$, Penicillin-streptomycin (50 I.U./ml), 0.1% DMSO and 0.16% AlamarBlue). Fluorescence is measured at time 0 on a fluorescent plate reader set to excite at 530 nM and measure emission at 590 nM. Explants are incubated in a normal air incubator at 28° C. Fluorescence will again be measured at 1, 2, 3, 4, 6, 12, and 24 h to measure change across time. At 24 h the tissue will be collected, weighed, and homogenized in lysis buffer (0.1 M phosphate buffered saline with 0.1% Triton X-100, PBST) for analysis of DNA using the Quant-iT PicoGreen dsDNA assay kit (Life Technologies, Inc.) to correct all samples for the number of cells. Fluorescence data will be corrected by either tissue weight or total DNA and expressed as change in fluorescence per mg tissue or μg DNA.

Fin cell isolation will be performed as previously described. Upon reaching confluence in a 3.5 cm petri dish, cells will be plated to confluence in a 96-well plate and the AlamarBlue assay will be performed as described for explants and corrected for total DNA within the well.

Skeletal Muscle Sampling and Explant/Cell Isolation: Skeletal muscle samples will be collected by needle (14G) biopsy in the anesthetized fish from which fin samples were collected. 2-5 mg skeletal muscle explants will be assayed in triplicate to assess metabolic rate by explant. Changes in fluorescence will be corrected for sample DNA.

Skeletal muscle stem cells (satellite cells) will be isolated from the remainder of the biopsy and grown to confluence. Upon reaching confluence satellite derived proliferating myoblasts will be plated into a 96-well plate and the AlamarBlue assay will be performed as described for fin cells. Alternatively, myoblasts may be stimulated to form nascent muscle fibers so that metabolic rate can be measured on the differentiated cell type.

Without wishing to limit the present invention to any theory or mechanism, it is believed that samples collected from fish that were determined to have a low metabolic rate as embryos will maintain a lower metabolic rate than samples collected from fish that had a high metabolic rate as embryos. FIG. 3 and FIG. 4B show that metabolic rate in explants and isolated cells can be accurately measured. It is believed that the metabolic rate from both skeletal muscle and fin samples can be accurately assessed. And, it is believed that the metabolic rate assessed from skeletal muscle samples will correlate with metabolic rate assessed from fin samples.

Data may be analyzed in SAS. The effect of embryo metabolic rate (high or low), adult body weight, and their interaction on metabolic rate from explants or cell will be assessed for each tissue type using a mixed model two-way ANOVA in SAS (SAS Inc., Cary, NC). Correlation analysis will be used to assess relationships between metabolic rate assessed by tissue type and sample type (cells or explants; Proc Corr). Regression analyses will be performed to quantitate this effect as needed.

The present invention may also be used to assess selection of brood stock based on metabolic rate of tissue samples, e.g., metabolic rate of explants from adult fish may be indicative of offspring metabolic rate. Future work may focus on this application in wild-caught brood stock.

Methods: Brood stock rearing and selection: 300 fish will be grown in a starter tank and moved as needed to maximally encourage growth and development. Feed will be provided 3 times daily to satiation. At 4 months of age, skeletal muscle or fin biopsies will be collected for metabolic rate determination as described and validated in Experiment 2. Fish will be tagged for identification and upon determination of metabolic rate, fish in the top and bottom 10% will be isolated and moved to other facilities.

Breeding: Brood stock in the high and low metabolic rate groups will be divided into five tanks with 6 brood stock in each tank (n=5). The mouths of female fish will be checked every week for embryonic fish. Embryos will be collected and assayed for metabolic rate as previously described. To prevent continuously sampling from the same female fish, a female that provides a clutch will be immediately removed from the study. Studies will continue until at least 2 clutches have been collected and analyzed from each tank.

A one-way ANOVA will be used to assess the effect of explant/cell metabolic rate on embryo metabolic rate. Tank will serve as the experimental unit (n=5). Accordingly, the single measurement of each embryo will be nested within brood and brood nested within tank. Power calculation mirrors that from experiment 1.

Without wishing to limit the present invention to any theory or mechanism, it is believed that the metabolic rate of explants from adult fish will be positively related to the offspring metabolic rate. This result would indicate that brood stock can be selected based on metabolic rate of adult tissue samples.

Example 2: Field Application

Example 2 is an example of the use of the methods and systems of the present invention. The present invention is not limited to the examples set forth in Example 2.

Example 2 describes procedures that allow for field application of the methods and systems of the present invention. For example, Example 2 describes assessing results of methods of the present invention using a controlled digital photograph, eliminating the requirement for a fluorescent spectrophotometer.

First, the quantitative assessment of color change from digital photographs will be compared to that obtained using a fluorescent plate reader, e.g., quantitated RGB color will be correlated with fluorescent signal measured on a plate reader. Without wishing to limit the present invention to any theory or mechanism, it is believed that the use of digital photographs may be an adequate substitute for a fluorescent plate reader, allowing the methods of the present invention to be performed in the field.

Methods: Plates are digitally captured using a 12 megapixel digital camera. In all pictures, a standard white background is used and a color reference chart is included to correct for potential differences in lighting. Using Adobe Photoshop eyedropper tool, the red, green, and blue color within each well will be quantitated (see FIG. 5, preliminary data). The red, green, and blue color intensity, differences between intensity of different colors (e.g. Red-Green), and ratios of color intensity (e.g. Red/Blue) are correlated with fluorescence to identify the color spectrum quantitation that best allows for quantitative analysis of metabolic rate from a color photo. Data may first be analyzed through XY plots using GraphPad Prism version 5.00 for Windows, GraphPad Software, San Diego California USA, www.graphpad.com to visually understand the relationship between fluorescence and each variable of color (intensity of a single color, differences, ratios). It is possible that linear relationships will be found, and thus Proc Corr in SAS (SAS Institute, Cary, NC) will then be performed to identify the factor with the greatest correlation with change in fluorescence. Proc Reg in SAS may be used to quantitate the relationship between fluorescence and quantitated RGB spectrum. If fluorescence and RGB values are not linearly related the data may be transformed (or a non-linear regression analysis may be performed).

Next, the possibility of shipping explants for analysis in a central lab will be assessed. Without wishing to limit the present invention to any theory or mechanism, it is believed that explants may retain their metabolic rate (e.g., fluorescence per mg tissue) for a period of time, e.g., 12 hr or more, after collection. Maintaining explants at 4° C. may extend viability.

Methods: The differences in the timing of assay initiation and sample incubation temperature will be compared to assess the possibility that explants could be collected on farm and shipped to a commercial laboratory for analysis. The present invention establishes that embryonic fish and oysters can be collected and shipped to a central lab for analysis, thus it may be possible for explants as well.

Within a fish, the coefficient of variation in metabolic rate of skeletal muscle and fin explants is low (5.7 and 6.2%, respectively). By collecting multiple samples from the same individuals, it may be possible to perform comparisons to thoroughly analyze the effects of assay timing and incubation temperatures on explant viability. This study will be conducted testing 5 different times (0, 6, 12, 24, and 48 h) and 2 different incubation temperatures (4 or 22 degrees C.).

Each condition will be run in triplicate within a fish. As such, 30 samples/fish are needed. To accommodate the need for this large number of samples/fish, samples will be collected immediately post-mortem from fish anesthetized in an ice water slurry and sacrificed by decapitation. Each sample will be placed in a capped culture tube containing 1 ml L-15 medium without phenol red supplemented with 25 mM HEPES, 5 mM $NaHCO_3$, Gentamycin (100 μg/ml), and fungizone (2.5 μg/ml). Three samples from each fish will be exposed to each condition. Samples maintained at both room temperature and at 4° C. will be kept in Styrofoam shipping containers within the lab and samples will be removed at 6, 12, 24, and 48 hours of incubation. At the end of the incubation samples will be analyzed as previously described for metabolic rate. At the conclusion of the study, explants will be weighed and total DNA within the sample will be assessed. Fluorescence data will be corrected by either tissue weight or total DNA and expressed as change in fluorescence per mg tissue or μg DNA.

Example 3: Additional Experiments

Figure 10A:
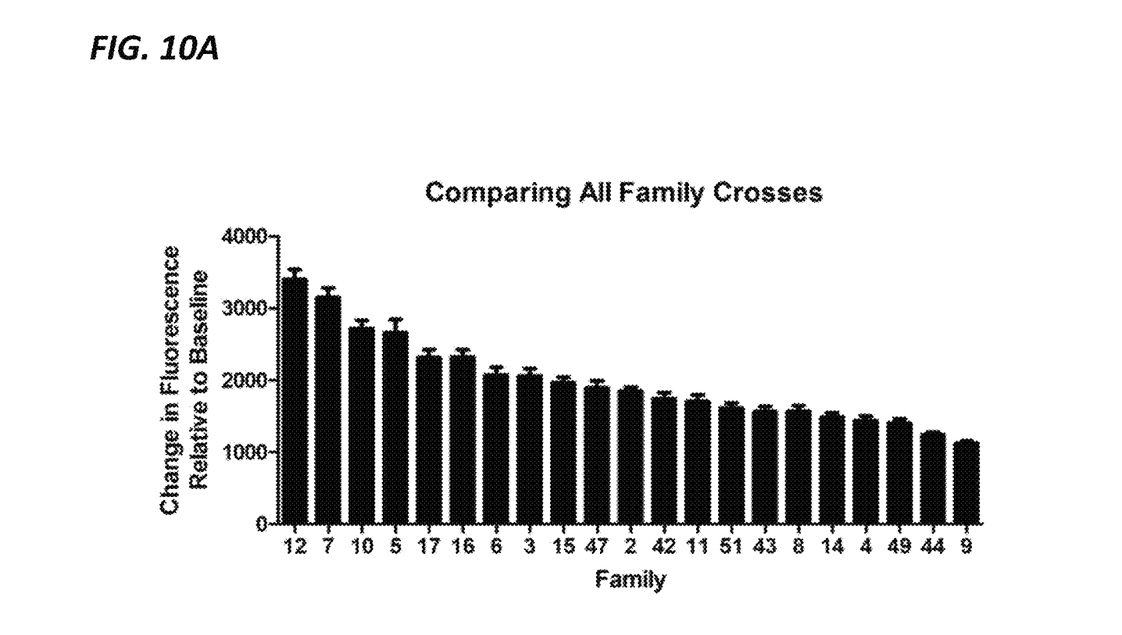
FIG. 10A shows that oyster spat derived from different families induced nearly 3 fold differences in AlamarBlue reduction. This suggests that significant variation in $NADH_2$ production exists between families.
Figure 10B:
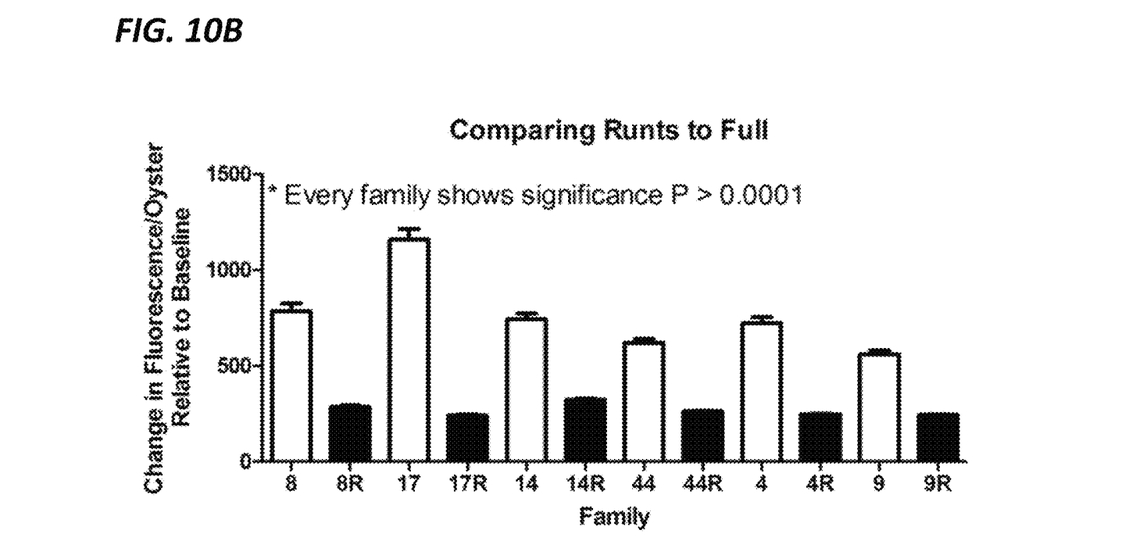
FIG. 10B shows that if oyster spat within a cross are size separated those spat that grow more slowly (runts; R) induce less signal that oysters that grow more quickly.
Figure 11A:
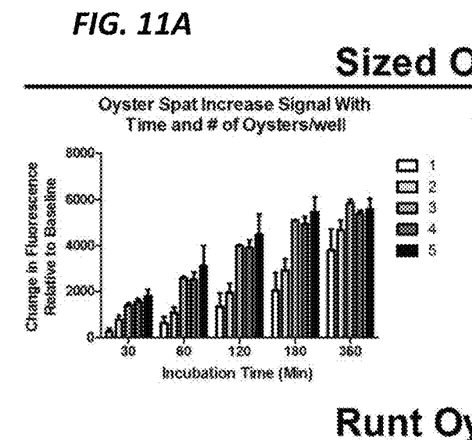
FIG. 11A-11D show that in both sized (FIG. 11A, FIG. 11B) and runt oysters (FIG. 11O, FIG. 11D) the signal generated increases with time and with the number of oysters within a well. Larger oysters (sized) generate signal more quickly and with fewer oysters than do runt oysters.
Figure 11B:
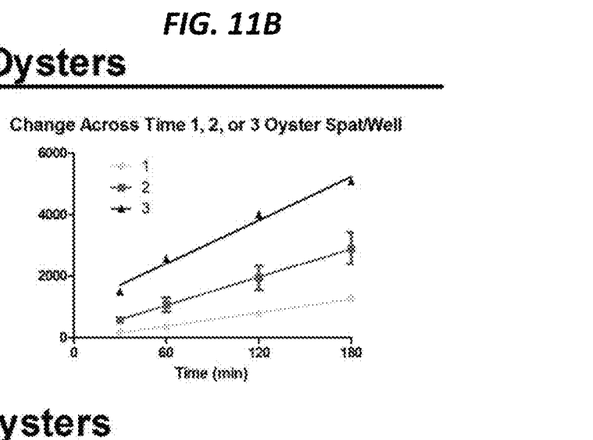
Figure 11C:
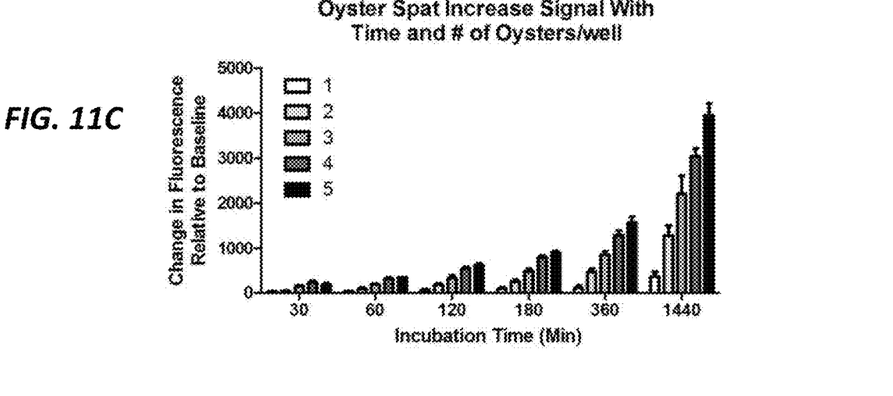
Figure 11D:
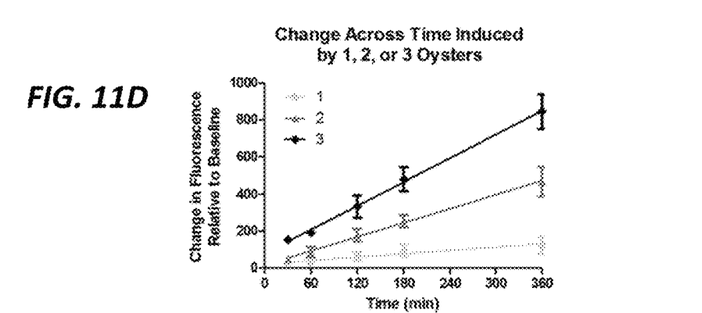
Figure 12:
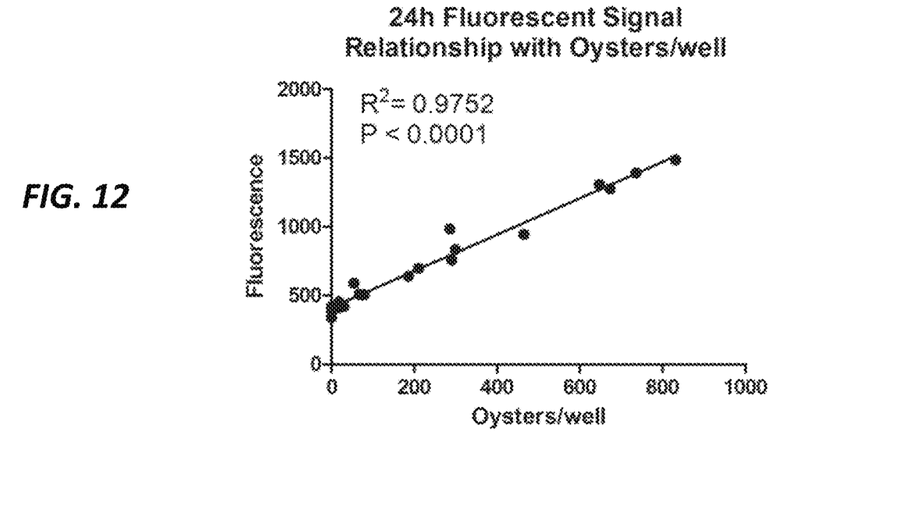
FIG. 12 shows D-larvae (2-day post fertilization larval oysters) increase the signal generated in this AlamarBlue based assay linearly as the number of larvae within a well increases ($R^2$=0.9752).
Figure 13A:
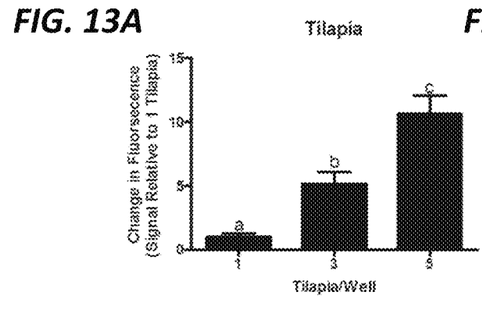
Figure 13B:
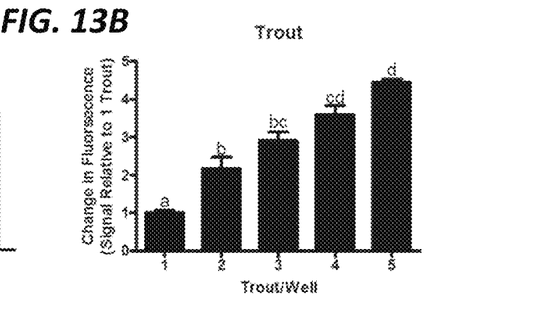
Figure 13C:
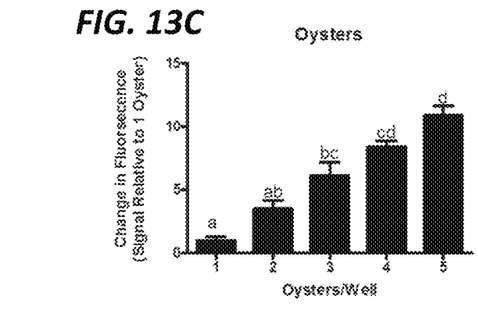
Figure 13D:
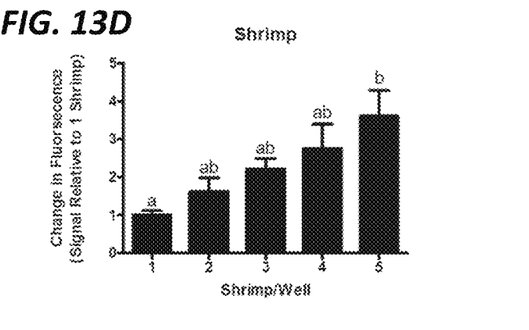
Figure 14:
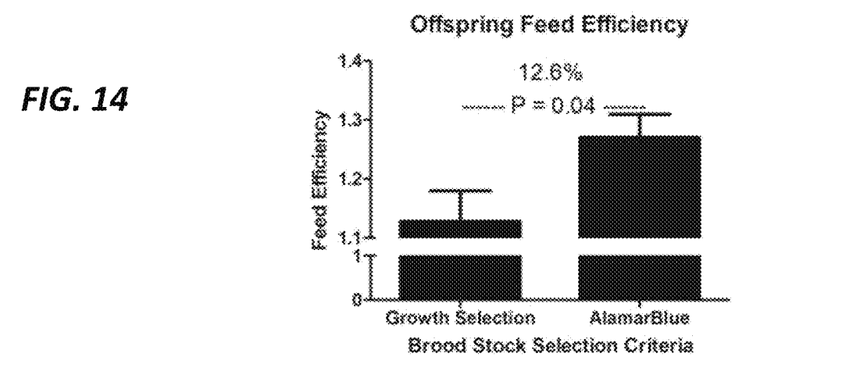
FIG. 14 shows that tilapia broodstock selection based on metabolic rate, as measured by the AlamarBlue based assay, results in offspring with higher feed efficiency than offspring from Tilapia broodstock selection based on growth.
Figure 15:
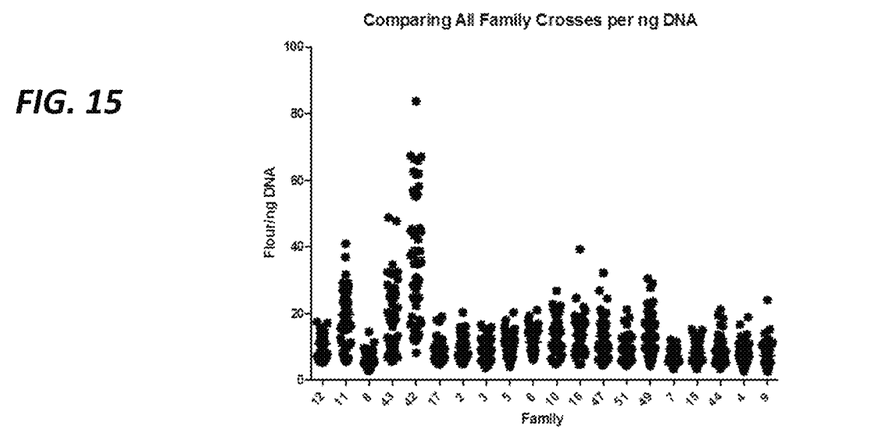
FIG. 15 shows the variability in metabolic rate within a family. This proposes that broodstock selection based on family selection will not improve genetics for growth nearly as rapidly as selection based on the individual metabolic rate.
Figure 16:
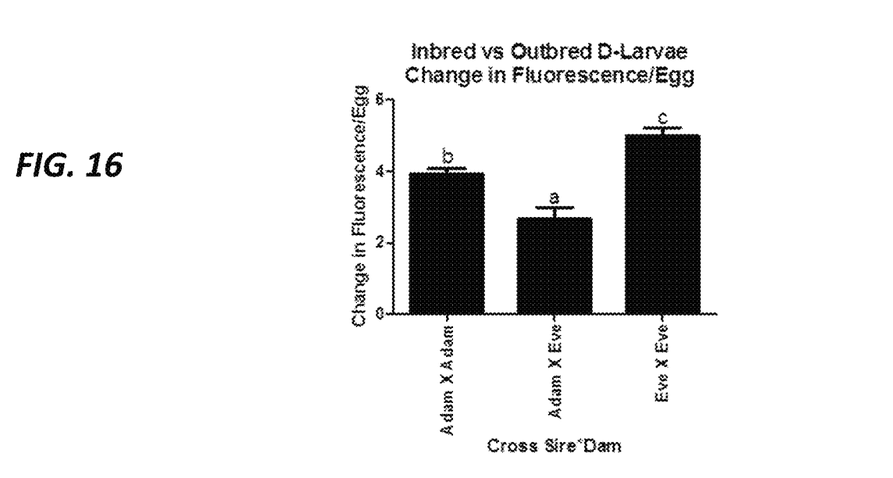
FIG. 16 shows that slow growing inbred oyster lines (adam X adam) and (eve X eve) have higher metabolic rates than their outcrossed faster growing half-siblings (adam X eve).

FIG. 10A-10B show representative results from Oyster Spat. The top figure shows that oyster spat derived from different families induced nearly 3 fold differences in AlamarBlue reduction. This suggests that significant variation in $NADH_2$ production exists between and within families. In the middle figure we can see that if oyster spat within a cross are size separated those spat that grow more slowly (runts; R) induce less signal that oysters that grow more quickly. FIG. 11A-11D show that in both sized and runt oysters the signal generated increases with time and with the number of oysters within a well. Larger oysters (sized) generate signal more quickly and with fewer oysters than do runt oysters. FIG. 12 shows D-larvae (2-day post fertilization larval oysters) increase the signal generated in this AlamarBlue based assay linearly as the number of larvae within a well increases ($R^2=0.9752$). FIG. 13A-13D show changes in fluorescence with various numbers of tilapia (FIG. 13A), trout (FIG. 13B), oysters (FIG. 13C), and shrimp (FIG. 13D). FIG. 13A-13D show that metabolic rate within a given volume increases as the number of individuals within that volume increases. FIG. 14 shows that tilapia broodstock selection based on metabolic rate, as measured by the AlamarBlue based assay, results in offspring with higher feed efficiency than offspring from Tilapia broodstock selection based on growth. FIG. 15 shows the variability in metabolic rate within a family. This proposes that broodstock selection based on family selection will not improve genetics for growth nearly as rapidly as selection based on the individual metabolic rate. FIG. 16 shows that slow growing inbred oyster lines (adam X adam) and (eve X eve) have higher metabolic rates than their outcrossed faster growing half-siblings (adam X eve).

REFERENCES

The disclosures of the following documents are incorporated in their entirety by reference herein: (1) Gjedrem, T., Aquaculture Research, 2000. 31(1): p. 25-33. (2) Conceicao, L. E. C., Y. Dersjant-Li, and J. A. J. Verreth, Aquaculture, 1998. 161(1-4): p. 95-106. (3) Gjerde, B., Aquaculture, 1986. 57(1-4): p. 37-55. (4) Huang, C. M. and I. C. Liao, Aquaculture, 1990. 85(1-4): p. 199-205. (5) Hulata, G., G. W. Wohlfarth, and A. Halevy, Aquaculture, 1986. 57(1-4): p. 177-184. (6) Tave, D. and R. O. Smitherman, Transactions of the American Fisheries Society, 1980. 109(4): p. 439-445.

(7) Thodesen, J., et al., Aquaculture, 2011. 322: p. 51-64. (8) Gadagkar, S. R., Social behaviour and growth rate variation in cultivated tilapia (*Oreochromis niloticus*). 1997, Dalhousie University: Dalhousie University. (9) Koebele, B., Environmental Biology of Fishes, 1985. 12(3): p. 181-188. (10) Blanckenhorn, W. U., Ethology Ecology & Evolution, 1992. 4(3): p. 255-271. (11) Seiler, S. M. and E. R. Keeley, Animal Behaviour, 2007. 74(6): p. 1805-1812. (12) Grant, J. W. A., Canadian Journal of Fisheries and Aquatic Sciences, 1990. 47(5): p. 915-920. (13) Huntingford, F. A., et al., Journal of Fish Biology, 1990. 36(6): p. 877-881. (14) McCarthy, I. D., C. G. Carter, and D. F. Houlihan, Oncorhynchus mykiss (Walbaum). Journal of Fish Biology, 1992. 41(2): p. 257-263. (15) Allee, W. C., et al., Journal of Experimental Zoology, 1948. 108(1): p. 1-19. (16) Magnuson, J. J., Canadian Journal of Zoology, 1962. 40(2): p. 313-363. (17) Purdom, C. E., Variation in Fish, in Sea Fisheries Research, F. R. H. Jones, Editor. 1974, Elek Science: London. p. 347-355. (18) BROWN, M. E., Journal of Experimental Biology, 1946. 22(3-4): p. 118-129. (19) Wohlfarth, G. W., Shoot carp. Bamidgeh, 1977. 29(2): p. 35-56. (20) Clarke, A. and N. M. Johnston, Journal of Animal Ecology, 1999. 68(5): p. 893-905. (21) Miyashima, A., et al., Aquaculture Research, 2012. 43(5): p. 679-687. (22) Cook, J. T., A. M. Sutterlin, and M. A. McNiven, Aquaculture, 2000. 188(1-2): p. 47-63. (23) Livingston, R. J., Journal of the Marine Biological Association of the United Kingdom, 1968. 48: p. 485-497. (24) Renquist, B. J., et al., Zebrafish, 2013. 10(3): p. 343-52. (25) Williams, S. Y. and B. J. Renquist, Journal of Visualized Experiments, 2015. In Press. (26) Smith, R. W. and D. F. Houlihan, Journal of Comparative Physiology B, 1995. 165(2): p. 93-101. (27) Brand, M. D., et al., Evolution of energy metabolism. Proton permeability of the inner membrane of liver mitochondria is greater in a mammal than in a reptile. Biochem J, 1991. 275 (Pt 1): p. 81-6. (28) El-Greisy, Z. A. and A. E. El-Gamal, The Egyptian Journal of Aquatic Research, 2012. 38(1): p. 59-66. (29) Siraj, S. S., et al. International Symposium on Tilapia in Aquaculture. 1983. Nazareth, Isreal: Tel Aviv University. (30) Palada-de Vera, M. S. and A. E. Eknath. Proceedings of the Fourth International Symposium on Genetics in Aquaculture. 1993. Wuhan, Hubei Province, China: Elsevier. (31) Mauger, R. E., P. Y. Le Bail, and C. Labbe, Comparative Biochemistry and Physiology B-Biochemistry & Molecular Biology, 2006. 144(1): p. 29-37. (32) Vanmeter, D. E., Progressive Fish-Culturist, 1995. 57(2): p. 166-167.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A method comprising:
   a) introducing a redox indicator to each individual in a pool of embryonic fish or juvenile aquatic organisms at T0:
   b) producing a selection of embryonic fish or juvenile aquatic organism by:
      i) measuring whole body metabolic rate of each individual in the pool of embryonic fish or juvenile aquatic organisms, wherein metabolic rate is measured using a colormetric/fluorescent redox assay comprising measuring a fluorescence value at time T0; measuring a fluorescence value at time T1 after time T0; and determining the change in fluorescence between T1 and T0 to determine a metabolic rate; and
      ii) selectively removing the individuals in the pool that had a metabolic rate in the 30%, 20%, or 10% highest metabolic rate of the pool from the remaining individuals in the group.

2. The method of claim 1, wherein embryonic fish or juvenile aquatic organisms are tilapia, trout, or zebrafish.

3. The method of claim 1, wherein individuals in the pool that had a metabolic rate in the 5% highest metabolic rates of the pool are separated from remaining individuals in the pool.

4. The method of claim 1, wherein the redox indicator comprises AlamarBlue®, reazurin, a tetrazolium dye, or PrestoBlue®.

5. The method of claim 1, wherein T1 is equal to T0 plus 8 hours, T0 plus 16 hours, or T0 plus 24 hours.

6. The method of claim 1, wherein measuring a fluorescence value comprises using a fluorescent plate reader.

7. The method of claim 1, wherein measuring a fluorescence value comprises obtaining a digital photograph of the cell sample and quantitating red, green, and blue color intensity, wherein the intensities are correlated with fluorescence to determine a quantitative measurement of metabolic rate.

8. A method comprising;
   a) introducing a redox indicator to each individual in a pool of mollusk at T0;
   b) producing a selection of mollusks by:
      i) measuring whole body metabolic rate of each individual in the pool, wherein metabolic rate is measured using a colorimetric/fluorescent redox assay comprising measuring a fluorescence value at time T0; measuring a fluorescence value at time T1 after time T0; and determining the change in fluorescence between T1 and T0 to determine a metabolic rate; and
      ii) selectively removing the individuals in the pool that had a metabolic rate in the 10% lowest metabolic rates of the pool from the remaining individuals in the group.

9. The method of claim 8, wherein the mollusks are oyster spat.

10. A system for preparing a selection of embryonic fish or juvenile aquatic organisms form a pool of embryonic fish or juvenile fish, said system measures whole body metabolic rate of each individual in the pool of embryonic fish or juvenile aquatic organisms; wherein metabolic rate is measured using a colormetic/fluorescent redox assay comparing introducing a redox indicator to the individual at time T0; measuring a fluorescence value at time T0; measuring a fluorescence value at time T1 after time T0; and determining the change in fluorescence between T1 and T0 to determine a metabolic rate; and produces a selection of embryonic fish or juvenile aquatic organisms by separating the individuals in the pool that had a metabolic tate in the 25%, 10%, or 5% highest metabolic rates of the pool from the remaining individuals in the group.

11. The system of claim 10, wherein the system processes 2,500 individuals in 8 hours.

\* \* \* \* \*